United States Patent [19]

Schlessinger et al.

[11] Patent Number: 4,546,770
[45] Date of Patent: Oct. 15, 1985

[54] PULMONARY MONITOR

[75] Inventors: Joseph E. Schlessinger, Berkeley; Richard G. Hamilton, San Francisco, both of Calif.

[73] Assignee: Critikon, Tampa, Fla.

[21] Appl. No.: 472,415

[22] Filed: Mar. 4, 1983

Related U.S. Application Data

[62] Division of Ser. No. 82,898, Oct. 9, 1979, Pat. No. 4,413,632.

[51] Int. Cl.⁴ .............................................. A61B 5/00
[52] U.S. Cl. ................................................. 128/630
[58] Field of Search ............... 128/630, 668, 670, 695, 128/709, 710

[56] References Cited

U.S. PATENT DOCUMENTS

| | | | |
|---|---|---|---|
| 2,647,508 | 8/1953 | Pglavin | 128/709 |
| 2,684,278 | 7/1954 | Marchand | 128/710 |
| 3,063,283 | 11/1962 | Polansky | 128/670 |
| 3,598,112 | 8/1971 | Figar | 128/630 |
| 3,745,407 | 7/1973 | Day | 128/710 |
| 3,871,362 | 3/1975 | Dunegan | 128/670 |
| 3,983,867 | 10/1976 | Case | 128/710 |

Primary Examiner—William E. Kamm
Attorney, Agent, or Firm—Mark A. Hofer

[57] ABSTRACT

A pulmonary monitor for measuring a complex set of variables utilizing a group of three pushbuttons arranged to operate in hierarchical a hierarchical pattern for facilitating operator control of the functions of the monitor.

2 Claims, 12 Drawing Figures

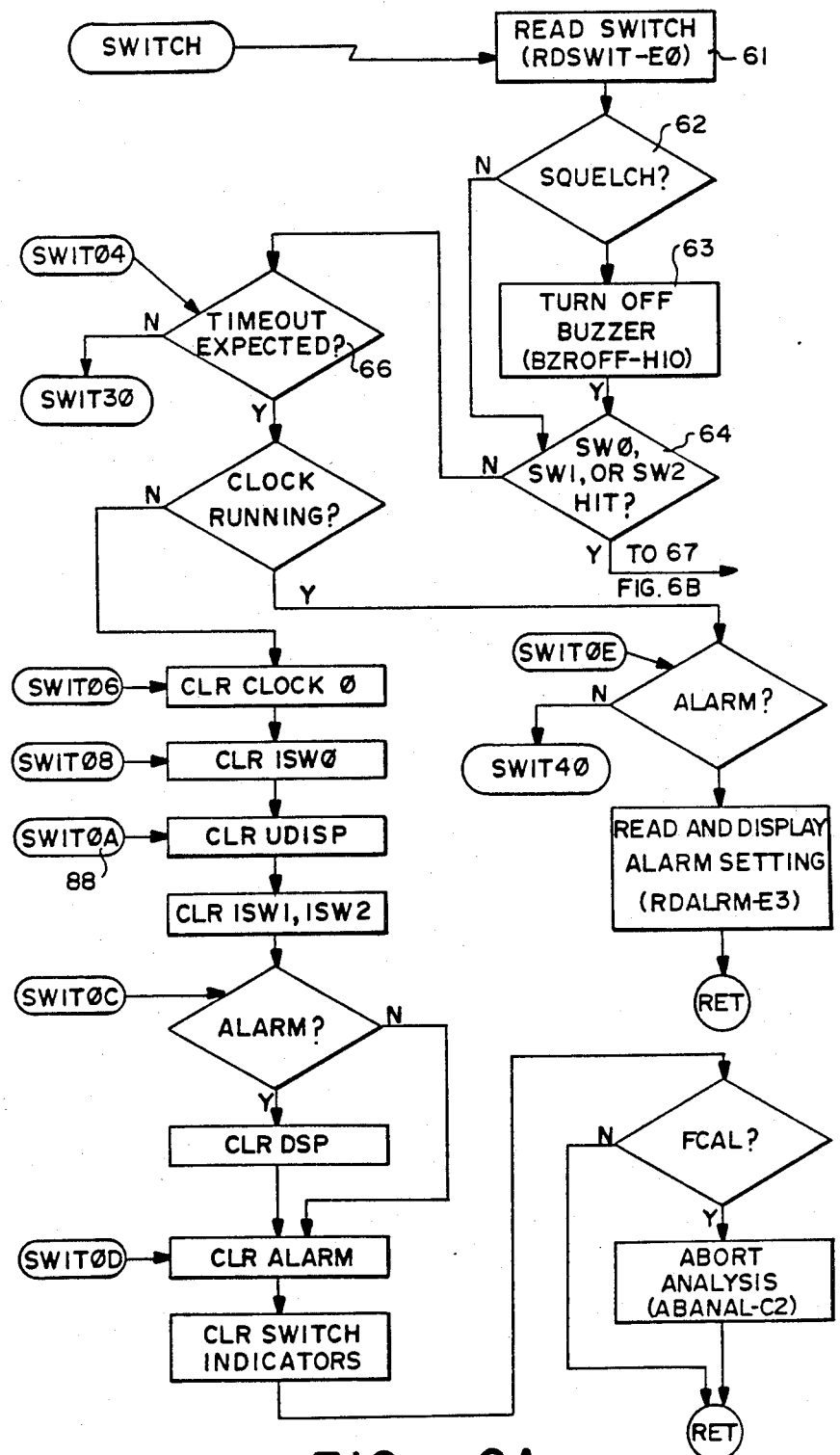
FIG.—6A

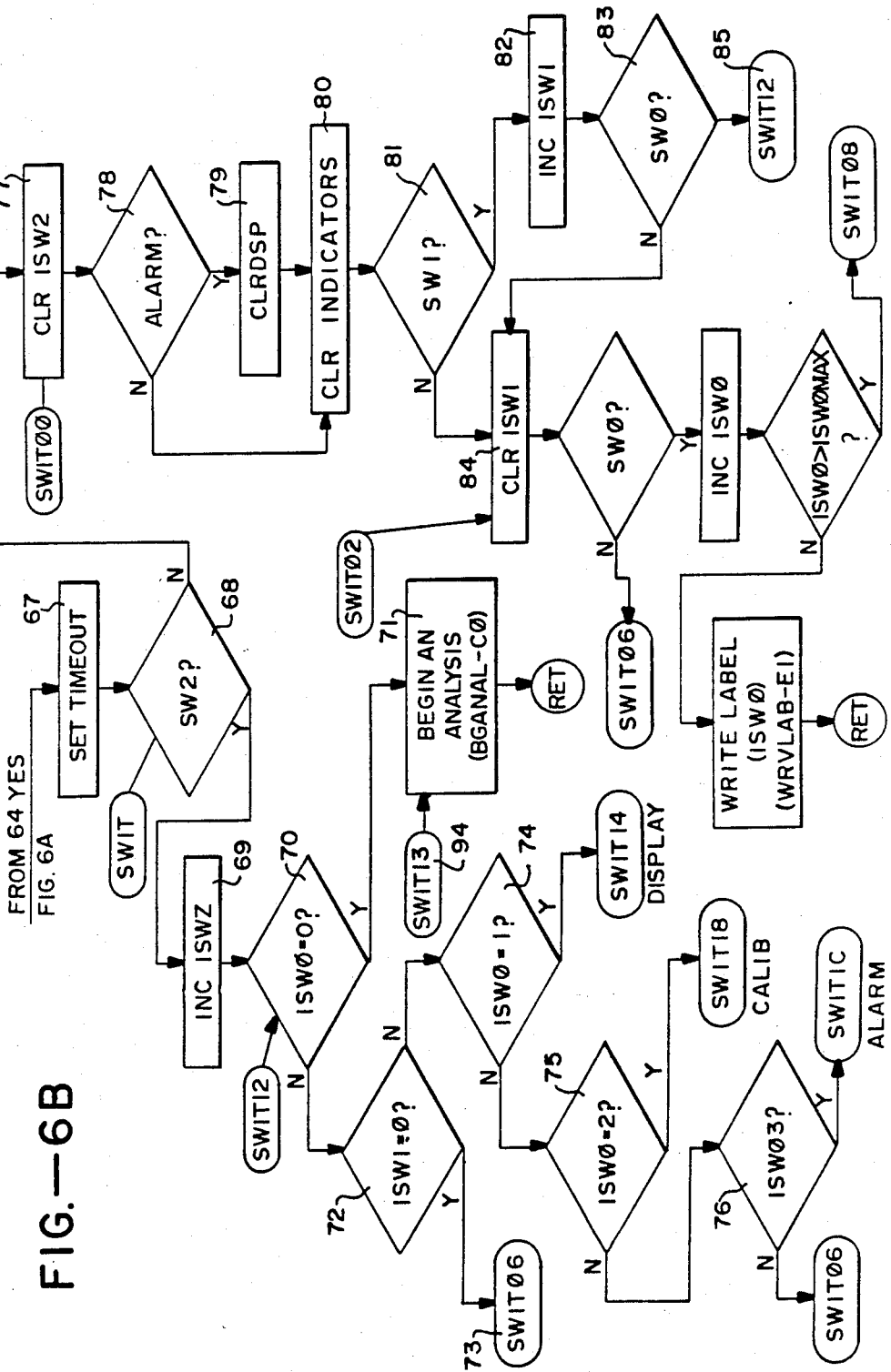
FIG.—6B

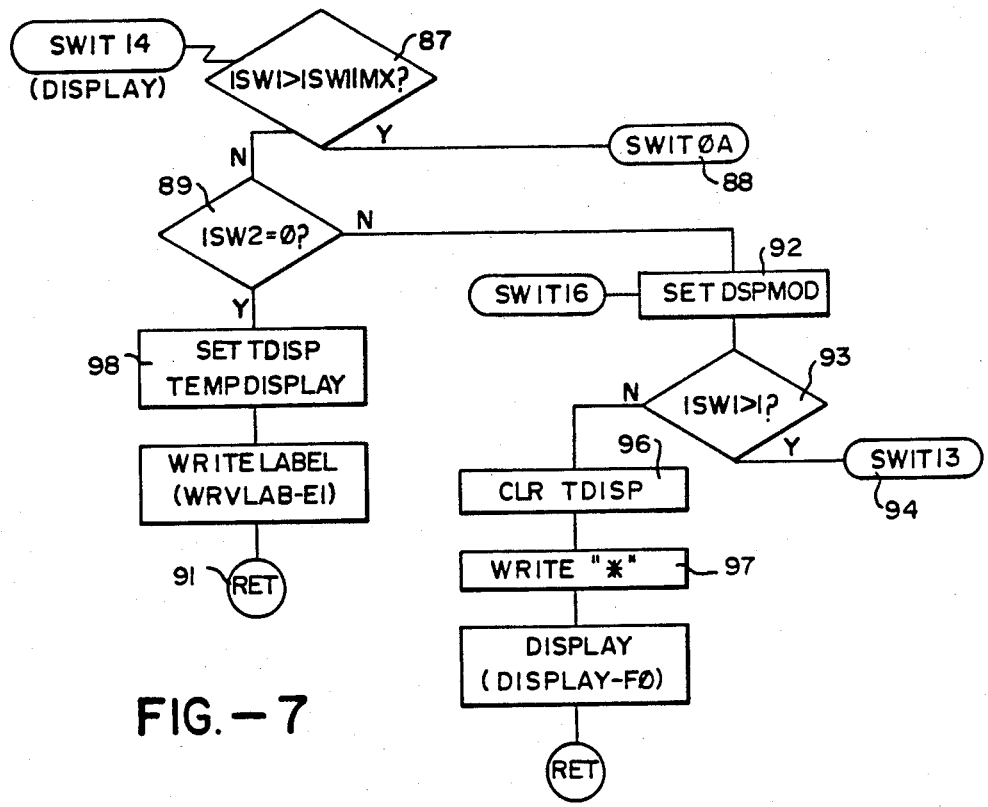
FIG.—7
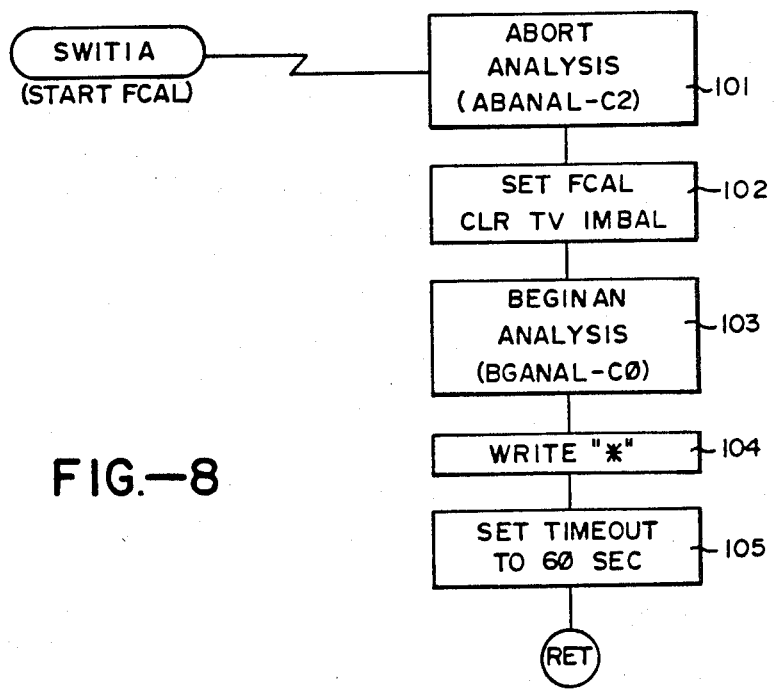
FIG.—8

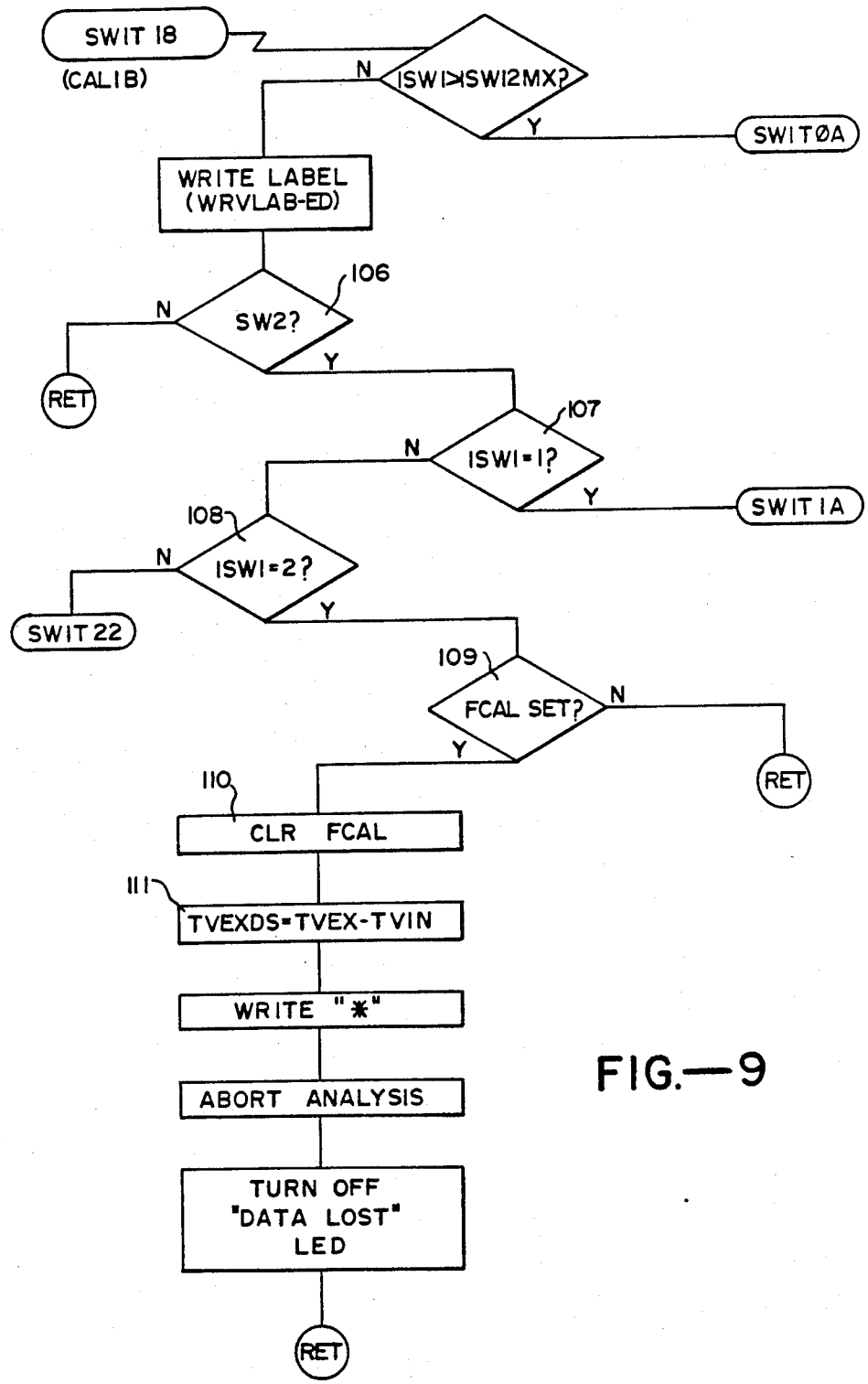
FIG.—9

4,546,770

PULMONARY MONITOR

This is a division of application Ser. No. 82,898, filed Oct. 9, 1979 now U.S. Pat. No. 4,413,632.

The present invention is directed to a hierarchical control system and more specifically to a pulmonary monitor for monitoring patients with respiratory difficulty.

In analyzing respiratory data for a patient, the monitoring system is preferably computerized. Processes using algorithmic procedures have been in use for many years. For example, a study project was conducted at the Institutes of Medical Sciences, Pacific Medical Center in San Francisco, Calif., which was supported by a National Institute of Health grant, HL 14740, and also by the IBM Corporation. This used an IBM 1800 computer to monitor many different parameters of a patient, including the respiratory parameters. As a result of that work, several algorithms were developed and used, at least for demonstration purposes, in a respiratory intensive care monitor Model 142 by the assignee of the present invention. However, this monitor had somewhat limited functions, while still being complex in operation.

It is therefore a general purpose of this invention to provide a hierarchical control system which can enable a human operator to easily interface with a system of complex variables.

A more specific object is a patient monitoring apparatus which can successfully monitor the several complex variables, including respiratory, cardiac, liver, gas analysis and others of a patient, while at the same time providing apparatus where the operator controls are simple and effective.

In accordance with the above objects, there is provided a measuring apparatus especially for use where a complex set of variables is being measured, and where at least some of these variables have limits which if exceeded indicate an abnormal condition. These measuring conditions also require frequent calibration. Such apparatus includes means for sequentially selecting successive control functions related to said set of variables, including limit control functions and calibration control functions. Second manual control means specifies a numerical limit for a selected variable of the limit control functions. Third manual control means executes the control functions. There is also included means for displaying the control functions.

FIGS. 6A and 6B are flow charts illustrating the operation of manual control buttons on the apparatus of the present invention.

FIGS. 7, 8, 9, 10 and 11 are flow charts of subroutines related to FIG. 6.

Figure 1:
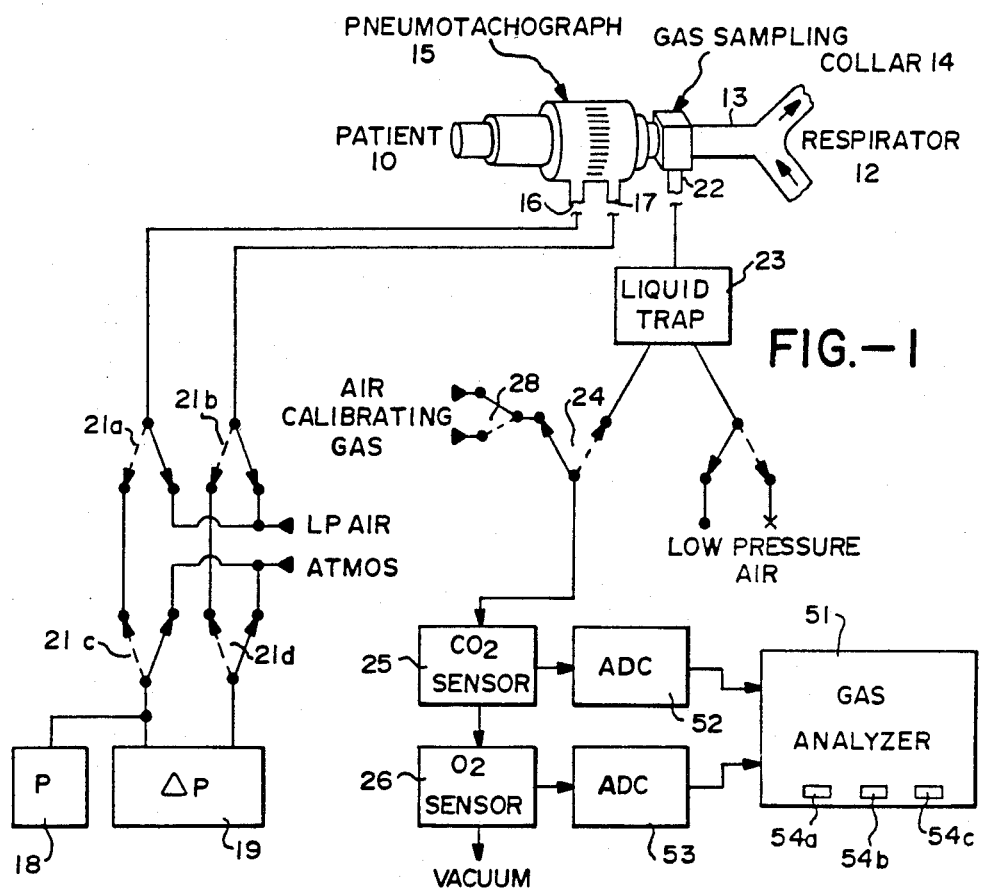
FIG. 1 is a block diagram illustrating the apparatus of the invention as it would be connected to a patient.

FIG. 1 illustrates the pulmonary monitoring device of the present invention as it would be connected to a patient along with a second gas analyzing device. A patient 10 is connected to a respirator 12 through a tube 13 which has both a gas sampling collar 14 and a pneumotachograph 15. Such pneumotachograph may be of the type shown in U.S. Pat. 4,083,245, assigned to the present assignee. Such device has a pair of orifices 16 and 17 with a resistance element between them across which a differential pressure occurs indicating the amount of flow of gas to or from the patient with the orifice 16 also providing an indication of the absolute pressure in the lungs. Such orifices 16 and 17 are connected to an absolute pressure transducer 18 and a differential pressure transducer 19 through the switches 21a through 21d. The dashed position of the switches is the measuring position with the solid line position being for the purpose of purging the pneumotachograph 15 with low pressure (LP) air.

A gas sampling collar 14 is connected through a gas sample line 22, a liquid trap 23, and through a switch 24 to an oxygen analyzer 26 and a carbon dioxide analyzer 25. These are series connected to each other and then to a vacuum as indicated. Liquid trap 23 is disclosed and claimed in a copending application Ser. No. 894,190 and now Pat. No. 4,197,858. Trap 23 is supplied low pressure air via a switch 27. Finally, for calibration and standardization purposes, switch 24 connects, through switches 24 and 28, a calibrating gas source and air to sensors 25 and 26.

Here, the gas sensors or analyzers 25 and 26 are connected to a gas analyzer unit 51 through analog to digital converters 52 and 53. Gas analyzer unit 51 includes a three push button group 54a, 54b, and 54c whose functions will be explained below.

Figure 2:
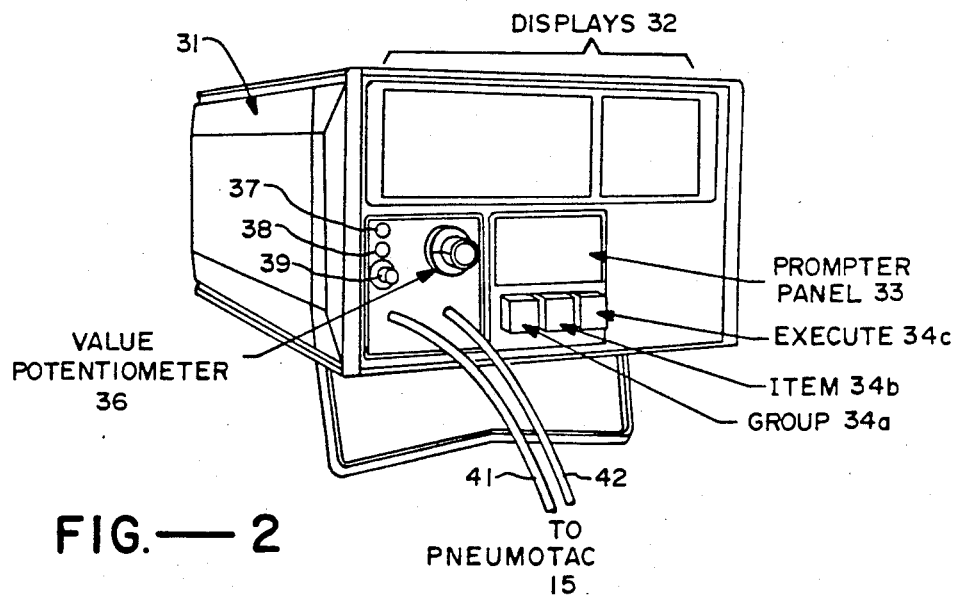
FIG. 2 is a perspective view of the present invention.

FIG. 2 is a perspective view of the actual pulmonary monitor which has a cabinet 31, a three-part LED display 32, a prompter panel display 33, GROUP, ITEM and EXECUTE push buttons 34a, b and c, a rotary value potentiometer 36, data loss indicator 27, alarm light 38, and alarm reset 39. In addition, there are a pair of plastic tubes 41 and 42 which are connected to the pneumotachograph at its orifices 16 and 17. Thus, referring to FIG. 1, the pressure transducers 18 and 19 and the various switches 21a through 21c are all internal to the instrument within cabinet 31.

Figure 3:
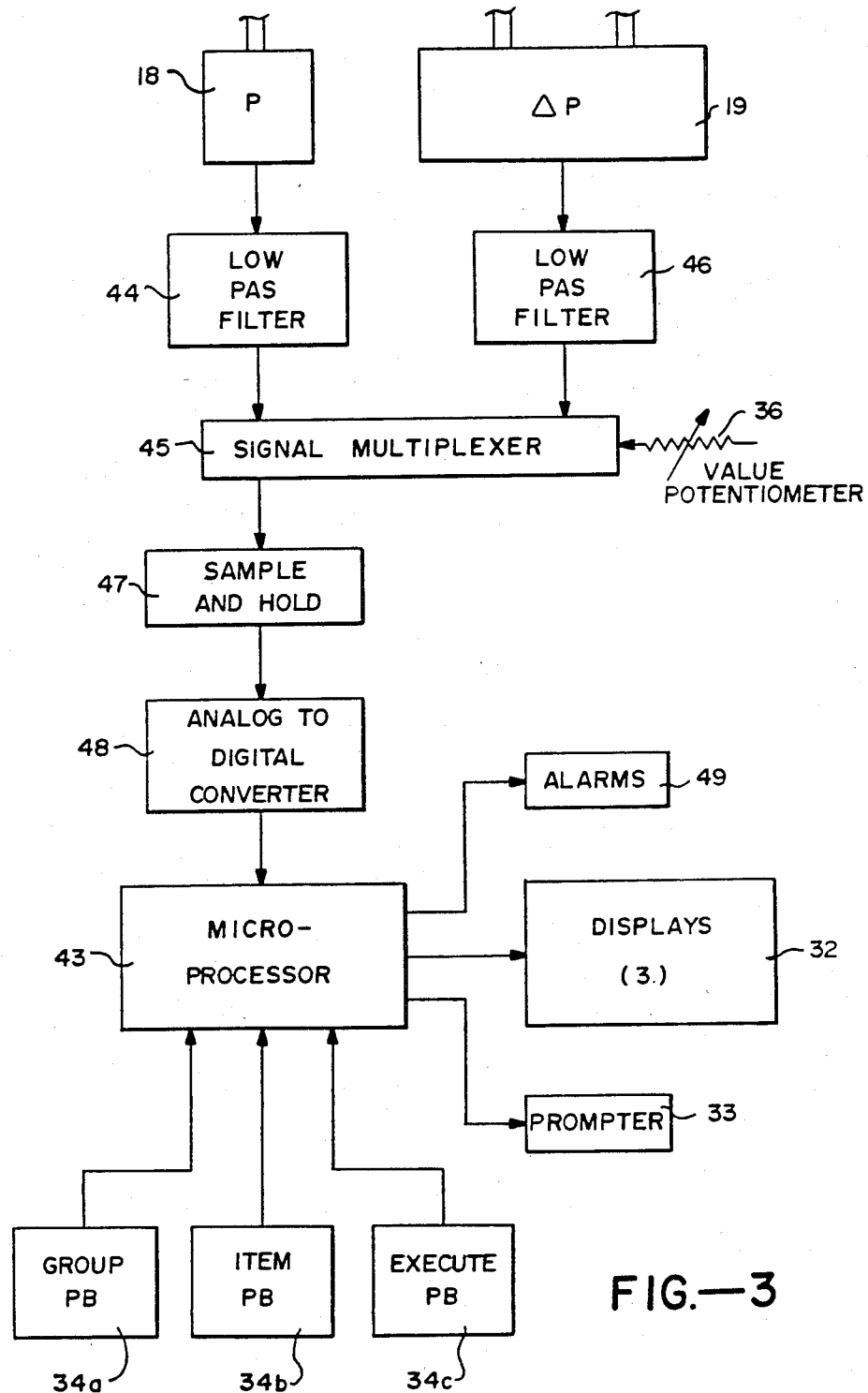
FIG. 3 is a block diagram embodying the invention.

FIG. 3 indicates the internal organization of the monitor of FIG. 1, where the pressure transducers 18 and 19 are connected to a microprocessor 43 by means of low-pass filters 44 and 46, a signal multiplexer 45, sample and hold unit 47, and analog-to-digital converter 48. Microprocessor 43 also receives the input value from the value potentiometer 36 via multiplexer 45 and senses input the number of times any of the push buttons 34a, 34b and 34c have been pressed. As outputs, the microprocessor drives the displays 32, the prompter panel display 33, and also an alarm unit 39 which provides both the visual alarm 39 (FIG. 2) along with audible alarms.

Figure 4:
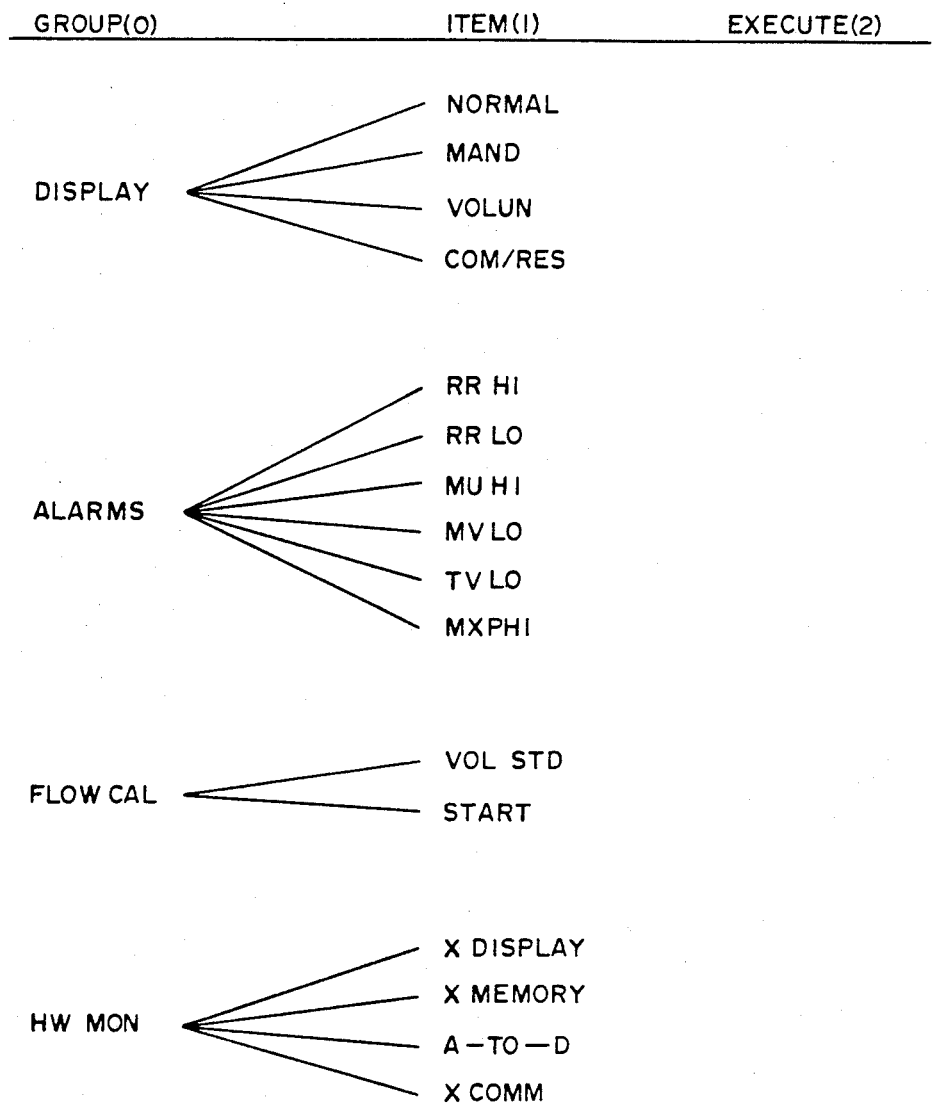
FIG. 4 is a chart showing the operation of one embodiment of the invention.
Figure 5:
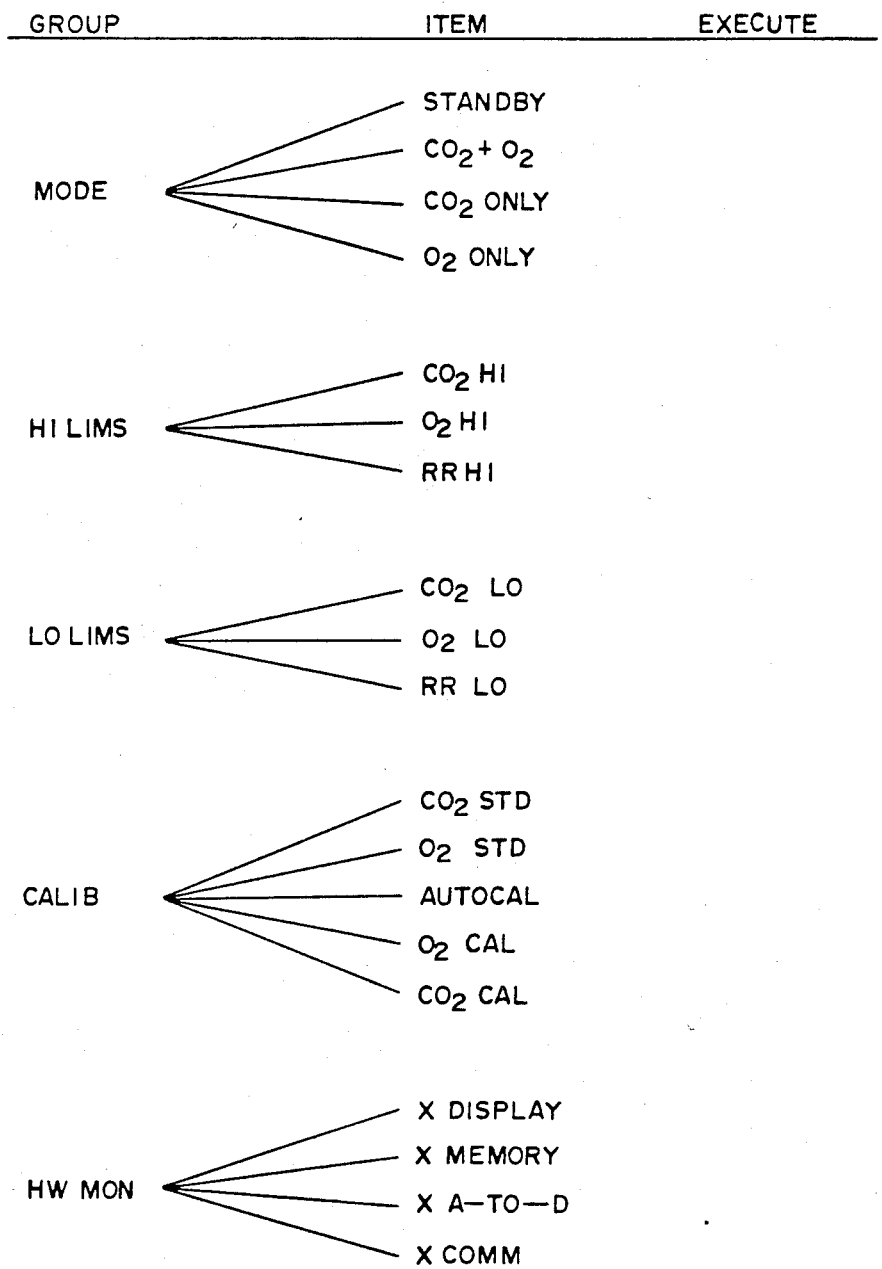
FIG. 5 is a chart showing the operation of another embodiment.

FIG. 4 illustrates the function of the push button switches 34a, 34b and 34c where they are designated GROUP, ITEM and EXECUTE. These switches, as indicated in FIGS. 4 and 5, are logically operated from left to right.

Referring to FIG. 4, the GROUP push button is pushed repeatedly until the desired mode of operation is achieved. This is either DISPLAY, ALARM, FLOW CALIBRATION, or HARDWARE MONITORING (HWMON). These group headings are displayed in a carousel or circular manner in the prompter panel 33 of FIG. 2. Then, the ITEM push button, 34b, is actuated to select one of the specific control functions within the control function group as listed on FIG. 4. Finally, the EXECUTE pushbutton 34c will implement the function in a manner to be described below.

The following are definitions of the abbreviations used in conjunctions used in FIG. 4:

mode. This allows the operator to select which variables of the system are displayed at various times in the machine cycle. The following table details what is displayed at the various times:

|  | ANALYSIS |  |  | 1ST HALF OF FLUSH |  | 2ND HALF OF FLUSH |  |  |
|---|---|---|---|---|---|---|---|---|
| NORMAL | TVIN | TVEX | MAWP | MAIP | RR | TVIN | TVEX | MV |
| MAND | TVIM | TVEM | MAWP | MAIP | RRM | TVIM | TVEM | MVM |
| VOLUN | TVIV | TVEV | MAWP | MAIP | RRV | TVIV | TVEV | MVV |
| CMP/RES | TVIN | TVEX | CMP | RES | WKIN | TVIN | TVEX | MV |

| ABBREVIATIONS USED | | |
|---|---|---|
| Name | Units | Meaning |
| TVIN | Liters | Tidal Volume Inspired |
| TVEX | Liters | Tidal Volume Espired |
| RR | Breaths/Min | Respiratory Rate |
| MV | L/Min. | Minute Volume |
| MAWP | Cm H$_2$O | Mean Airway Pressure |
| MAIP | Cm H$_2$O | Maximum Inspiratory Pressure |
| CMP | L/100 Cm H$_2$O | Compliance |
| RES | CM H$_2$O/(L/sec) | Resistance |
| WKIN | C-M/Min | Work of Inspiration |
| TVIM | | |
| TVEM | | As above, for Mandatory Breaths |
| RRM | | |
| MVM | | |
| TVIV | | |
| TVEV | | As above, for Voluntary Breaths |
| RRV | | |
| MVV | | |

Similarly, and referring to FIG. 1, when a gas analyzer device is used, FIG. 5 shows the carousel display of the GROUP, ITEM, and EXECUTE push buttons 52a, 52b and 52c. In general, and referring to both FIGS. 4 and 5, this type of hierarchical or "tree" command structure allows for monitoring of complex physiological variables under adverse ambient conditions. For example, because of the moisture and mucous of the breath of the patient, calibration must be carried on and the hardware of the device checked for proper operation. In addition, since these conditions or variables have limits which if exceeded indicate a pathological condition, alarms with effective limits are also provided. Moreover from a broader standpoint this type of system might also be used for variables involving wind, temperature or acidity for example.

From an operational standpoint, the GROUP and ITEM push buttons may be thought of as a functional unit to allow the GROUP and ITEM "menu" to be inspected. Of course, these are displayed circularly in a carousel fashion. But, to implement any function, the EXECUTE push button must be pressed.

Now referring specifically to the pulmonary monitor of FIG. 2, and its command tree of FIG. 4, the device operates on a 40-second cycle. The first 20 seconds of the cycle is the analysis period, during which the monitor collects data from the patient and displays current tidal volume in the two left hand portions of display 32. The analysis period is followed by a 20 second flush period, during which period the pneumotachograph lines are backflushed with dry air to prevent condensation. During this 20 second flush period, all displays are averages calculated over the previous analysis. In other words, during the analysis, there are displayed breath by breath numbers, and during the flush period (which is divided into two 10 second halves) there are averages derived from the previous analysis. Thus the first group of specific control functions accomplished is a display As is clear from the above table, the four display modes are NORMAL, MANDATORY, VOLUNTARY and COMPLIANCE/RESISTANCE. Thus, for example, if the mandatory mode is selected, then the mandatory tidal volume in and mandatory tidal volume out are displayed in the two left display portions of the display 32 of FIG. 2. Also, during the first half of the flush and the second half of flush, all three portions of display 32 provide the information as indicated, and as defined by the above list of abbreviations.

Mandatory ventilation is defined as breaths in which the airway pressure rises during inspiration, indicating that they were driven by the respirator. Voluntary respiration is defined as breaths in which the airway pressure does not rise during the inspiration, indicating that the patient is breathing by himself. In both the normal and mandatory display modes, the breaths displayed correspond to those conditioned by a respirator or ventilator. In the compliance/resistance mode of operation, the work of inspiration (WKIN) is displayed. It is the work done by the respirator inflating the patient's lungs.

The next group is ALARMS, still referring to FIG. 4, which contains six items. These are all limit alarms. Thus, thresholds can be set by means of the value potentiometer 36 is FIG. 2, or alternatively are determined by the program of the microprocessor. For example a threshold might be set for a high respiratory rate (RR HI). Here, when the patient's respiratory rate exceeds the high limit, an alarm condition occurs. A noise and light is flashed, and a message is sent out over a network to be logged and to appear on a terminal. The alarm limits are those thresholds beyond which an alarm will occur. Such alarm limits are: (1) high respiratory rate (RR HI); (2) low respiratory rate (RR LO); (3) minute volume high (MV HI); (4) minute volume low (MV LO); (5) tidal volume low (TV LO); and (6) maximum pressure high (MXP HI). Examining the alarm tree of FIG. 4, it is obvious that the respiratory and minute volume alarms are in pairs. Thus, with respect to respiratory rate, if the patient is breathing too quickly, this means that he is breathing too shallowly—i.e., hyperventilating. The patient can also breathe the same amount of air, but if he is breathing it too quickly, then he is not getting sufficient gas exchange. If he is breathing very deeply but too slowly, he can be depleting his carbon dioxide. The minute volume high and low alarms indicate whether the patient is getting sufficient ventilation. That is, is enough gas passing into his lungs. The pressure high indicates whether the ventilator is exceeding a reasonably high pressure, thus making the patient uncomfortable.

In operation, as the ITEM push button is pressed, the current value of the alarm unit is displayed. If any of those display values is desired to be changed, then the EXECUTE button is pressed, and the display will then change to the current value of the value potentiometer 36. At this time, the value potentiometer may be rotated to change the alarm setting to a a desired value. And when a different branch is gone to, the alarm setting is stored in the memory of the microprocessor.

Still referring to FIG. 4, in the flow calibration group this tree structure includes as a first item the volume standard (VOL STD) which is the size of the syringe, for example 500 ml., which will be connected to the patient input of the pneumotachograph. However, the size of the syringe may be changed by rotating the value potentiometer 36. Next, the ITEM button is pressed to rotate START into view, and the EXECUTE button hit, after which the syringe is pumped in and out. The nominal tidal volumes that are being produced will be shown on the prompter panel. If the nominal values are close enough to within 20% of the volume standard that has been entered, the machine will accept the calibration as good, and store the new calibration factor as good. If not, it will reject this and keep whatever calibration was previously entered in the machine. If there is no calibration at all stored, the apparatus will not let any execution take place. There must be a valid calibration before any analysis is enabled.

The specific calibration procedure which is conducted under the control of the mocroprocessor 43 is the same as used in conjunction with the IBM 1800 technique. This is done as follows:

For the airway flow, the output level of the analog-to-digital converter (adc units) at zero flow (with the sample valves closed) is sampled for 0.4 seconds, averaged and stored as the zero offset. Airway flow is gain calibrated by pumping air from a syringe of known volume through the pneumotachograph. The computer samples and integrates the flow to obtain volume. When it has found enough full cycles or "breaths", it adjusts the flow gain by taking the ratio of the average volumes calculated to the volume of the syringe. The volumes in and out are also checked for consistency and balance. The zero calibration for flow drifts during the course of the day. Computer controlled pneumatic lines open the transducers to room air when patient data is not being collected. Prior to switching the pneumatic lines to sample the patient's airway, the computer samples the zero flow output of the transducer in order to determine the current zero offset.

The last group, the hardware monitor group, is a technique which exercises the various pieces of hardware on the apparatus to insure that they are all working properly. It allows the operator to examine all displays (X DISPLAY) to ascertain that the program memory is intact and the the read/write memory can read and correctly report data written into it (X MEMORY), that the analog to digital (A/D) converters are all working, that the span on the transducers is correct (X A-TO-D), and that the network is intact (X COMM). Such a network would include, for example, the gas analyzer or a display report processor which displays graphically information being collected, logs it, and prints reports.

The remaining algorithms used to provide for the indications discussed above were accomplished by large scale computer, the IBM 1800. And these techniques are accomplished as follows:

The flow through the pneumotachograph is chosen as the signal to use in indentifying the beginning of inspiration and expiration because it is the most likely to be present and it has fast response. Airway pressure is not used because it is not present for patients breathing spontaneously nor for the mechanical pumps and syringes used for test measurements.

Finding the beginning of a respiratory half-cycle would be easy if the flow remained positive throughout inspiration, crossed zero at the start of expiration and remained negative until the next inspiration began. However, patients usually have periods at the end of a half-cycle when the flow crosses zero many times. Both the volume and the time of this oscillating period belong to the half-cycle being completed; the new half-cycle begins when there is significant flow in the opposite direction.

Thus a minimum volume criterion is used. The smallest acceptable volume for the patient is stored; usually 100 ml for adults 25 ml for small children. The algorithm is implemented as follows. Instantaneous flows are accumulated or integrated so long as they do not cross or equal zero. When flow changes sign, a test is made for a minimum flow sum or volume. If the measured volume is greater than the established minimum, the previous flow zero-crossing is said to be the beginning of the breath half-cycle. If the volume does not meet this criterion, it is added to the previous imcomplete half-cycle volume. Since its volume is of opposite sign, it slightly decreases the total volume.

The symbols used for the respiratory variables and the required input signals are shown in the following table. All variables are the result of averaging the values computed over all appropriate breath half-cycles. The following notation is used:

f . . . Indicates flow
p . . . Indicates pressure
o . . . Indicates $PO_2$
c . . . Indicates $PCO_2$
I . . . Indicates inspiration
E . . . Indicates exipration
i . . . Subscript ranging over all inspiratory or all expiratory points
j . . . Subscript ranging over all inspirations or expirations
k . . . Number of sample points in all inspirations
l . . . Number of sample points in all expirations
m . . . Number of inspirations
n . . . Number of expirations.

Respiratory rate (RR) is simply the sampling rate (S) over the number of points in the average breath, where:

$$RR = \frac{S}{\frac{k}{m} + \frac{l}{n}} \tag{1}$$

$$breaths = \frac{\frac{pts}{min}}{\frac{pts}{breaths} + \frac{pts}{breaths}}.$$

Tidal volume (TV) of a half-cycle is the integral of flow and is obtained by summing flow over inspiration or expiration and multiplying by a volume conversion factor ($C_v$) which is the product of the sample interval ($\Delta t$), flow gain ($gain_f$).

$$C_v = gain_f \cdot \Delta t \tag{2}$$

$$\frac{ml}{adc} = \frac{1}{\frac{adc}{ml/sec}} \cdot sec \cdot 1$$

-continued $$TVIN = \frac{\Sigma f_i}{m} \cdot C_v$$

$$\frac{ml}{breath} = \frac{adc}{breath} \cdot \frac{ml}{adc}$$

The minute volume is the expired tidal volume times the rate, converted to liters.

$$MV = TV_E \cdot RR \cdot \frac{1}{1000} \quad (3)$$

$$\frac{liters}{min} = \frac{ml}{breath} \cdot \frac{breaths}{min} \cdot \frac{1}{ml/liter}$$

The maximum airway pressures (p') for all inspirations are averaged.

$$MXIP = \frac{\Sigma p'_j}{m} \cdot \frac{1}{gain_p} \quad (4)$$

$$cm\ H_2O = adc \cdot \frac{1}{\frac{adc}{cm\ H_2O}}$$

Positive end-expiratory pressure is taken as the lowest non-negative pressure (p'') during the period starting 320 ms prior to the end of expiration and ending 256 ms later.

$$PEEP = \frac{\Sigma p''_j}{n} \cdot \frac{1}{gain_p} \quad (5)$$

Mean airway pressure is the average pressure over the entire respiratory cycle.

$$MAWP = \Sigma p_i \frac{1}{k+l} \cdot \frac{1}{gain_p} \quad (6)$$

Instantaneous power is obtained by multiplying flow by pressure. The work of inspiration is calculated by summing power over inspiration for each breath, and adjusting to a minute rate. Because the airway pressure rather than the intra-pleural pressure is measured, the work calculated is that performed by the respirator and is an indication of the work which the patient would have to do if he were removed from the ventilator. All airway pressures are made relative to the PEEP value for the previous expiration before being multiplied by flow.

$$WKIN = \frac{\Sigma[f_i \cdot (p_i - p''_j)]}{m} \cdot C_v \cdot \frac{1}{gain_p} \cdot RR \cdot \frac{1}{100} \cdot 1 \quad (7)$$

$$\frac{g \cdot m}{min} = \frac{adc \cdot adc}{breaths} \cdot \frac{ml}{adc} \cdot \frac{1}{\frac{adc}{cm\ H_2O}} \cdot$$

$$\frac{breaths}{min} \cdot \frac{m}{cm} \cdot \frac{g}{ml}$$

Compliance and resistance are computed for each inspiration using a least squares fit on the model P=V/C+R·F. The respirator pressure is measured, and the computed compliance is that of the lung plus the chest wall. Pressures must be relative to PEEP, as in the work calculation.

The values $r_j$ and $c_j$ are computed for each inspiration, using the following equations to do a least squares error determination of r and c to fit the data to the model.

$$r_j = \frac{\Sigma v_i f_i \Sigma v_i p_i - \Sigma v_i p_i \Sigma v_i^2}{\Sigma v_i f_i \Sigma v_i f_i - \Sigma f_i^2 \Sigma v_i^2}$$

$$c_j = \frac{\Sigma v_i^2}{\Sigma v_i p_i - r_j \Sigma v_i \Sigma f_i}$$

Averages are then taken.

$$RES = \frac{\Sigma r_j}{m} \cdot gain_f \cdot 1000 \cdot \frac{1}{gain_p} \quad (8)$$

$$\frac{cm\ H_2O}{liter/sec} = 1 \cdot \frac{adc}{ml/sec} \cdot \frac{ml}{liter} \cdot \frac{1}{\frac{adc}{cm\ H_2O}}$$

$$CMP = \frac{\Sigma c_j}{m} \cdot gain_p \cdot C_v \quad (9)$$

$$\frac{ml}{cm\ H_2O} = 1 \cdot \frac{adc}{cm\ H_2O} \cdot \frac{ml}{adc}$$

The flow chart of FIG. 6 describes an event that happens once a millisecond. In essence, this flow chart keeps track of the three push button panel switches and executes the switch commands. In READ switch step 61, the push buttons 34a, 34b and 34c on the front panel are polled and asked if there are any new switches which have been hit. The switches are GROUP, ITEM and EXECUTE, and these are given in FIG. 6 the designations SWITCH ZERO, SWITCH ONE and SWITCH TWO. The SQUELCH and BUZZER steps 62 and 53 are for turning off an audible buzzer.

The next step 64, asks if any of the switches 0,1 or 2 have been hit. If the answer is no, then a branch designated switch 4, step 66, is gone to, which asks whether it has been 20 seconds since any switch has been hit. If it has been more than 20 seconds, then the prompter display panel is cleared, along with any temporary conditions. Thus, if a switch is hit and nothing more is done, for example an EXECUTE push button pressed, eventually the machine will clear itself and revert to its normal state where the prompter display will clear.

However, if one of the switches has been hit, in step 64 the switches are processed backwards from right to left; that is the EXECUTE first, then the ITEM, then the GROUP. This is of course the reverse of their actual operation logically, which is from left to right, i.e., GROUP, ITEM, and EXECUTE. Thus, the first question asked in step 64 is "was switch 2 hit?" The next step is a time-out step, 67, and then a branching step in 68 which, if switch 2 was hit, routes the hit through an incrementing step 69 to step 70 which asks if switch 0 was set. Switch 0, of course, is the GROUP switch, which if it is equal to zero is in a non-operative state, and then for DISPLAY a "1" state, ALARMS a "2" state, FLOW CALIBRATION a "3" state, and HARDWARE MONITORING a "4" state. Thus, if switch 0 was not set, or rather is zero, then in step 71 hitting switch 2 causes a new analysis start. If switch 0 was set to one of the four other modes discussed above, then the following will occur:

In step 72, the question that is asked is "is switch 1, the ITEM switch, equal to zero." If so, this indicates that the hardware mode designated switch 6 (step 73)

must be gone to. However, if the ITEM switch 1 is not equal to zero, then the four possible modes of DISPLAY, ALARM, FLOW CAL and HDW MON are branched to in step 74 with respect to switch 14, step 75 with respect to switch 18, step 76 with respect to switch 1C, and then implicitly the switch 06 indicating the hardware mode.

Next, referring back to step 68, if the switch 2 EXECUTE push button is cleared, step 77 is gone to. Next, in step 78, the question is asked whether by turning the value potentiometer 36 (FIGS. 2-3) we are entering an alarm, or changing the alarm value. If an alarm was being entered, the display is cleared in step 79. If one was not being entered, indicators are cleared in step 80, and in step 81 the question is "was switch 1, the ITEM switch, hit?" If the answer is yes, then in step 82, a counter is incremented which contains the current value of switch 1. Next, in step 83, the question is asked, "was switch 0 set to some value?" If the answer is no, then the front panel display is cleared via the branch beginning with step 84. If the answer is yes, then switch 12 (step 85) is gone to. It is time to execute a new display.

FIG. 7 illustrates branch switch 14 which is the result of step 74 which is related to the DISPLAY mode. It is for the purpose of executing one of the four ITEM choices of DISPLAY. This branch is gone to, because switch 0, that is the GROUP switch, was set to "1", as indicated in step 74 and the ITEM switch was set at some non-critical value. Switch 2 has been hit. In step 87, the question is asked "whether switch 1 (ITEM) is in a legal value" that is between 1 and 4. If not, then switch A is gone to (step 88, FIG. 6) which clears the display and resets switch 0 to zero. In other words, this switch position is the effective blank that occurs in the wrapping around of the carousel which includes, referring to FIG. 4, NORMAL, MANDATORY, VOLUNTARY and COMPLIANCE/RESISTANCE. On the other hand, if switch 1 was a legal value, then in step 89 the question is asked "is switch 2 equal to zero." If so, then again this is an effective blank, and a return is made after clearing as indicated in step 91. However, if switch 2 was not zero, then an indicator is permanently set, indicated by step 92, which has the effect of determining what is going to be displayed during analysis, and what is going to be displayed during flush. If switch 2 has been hit twice, then the second time, that is to say the most recent time, as indicated in step 93, it starts a new analysis as indicated by the switch 139 (designated 94) which is also an input to step 71 (FIG. 6). However, if it is not greater than one, then as indicated in step 96 the display is cleared, in step 97, a star (*) is written which indicates an execution and a return is made as indicated.

The display mode, illustrated in FIG. 7, also has the advantage that, as for example in step 98 which is a temporary display step, where no execution is desired, then after 20 seconds a display will be produced where the ITEM switch has been activated.

FIG. 8 illustrates the flow calibration mode, switch 1A, which is initiated by being in START for the ITEM category (see step 107 of Fig. 9). In step 101, any analysis is aborted, in step 102 a flag is set, and in step 103, a special flow calibration analysis is begun. Next, in step 104, a star (*) is written as the leftmost character of an 8-character display. And finally, in step 104, a time-out of 60 seconds is set.

Referring now to FIG. 9, with switch 18 (see step 79, FIG. 6, this deals with the calibration to correct for tidal volume imbalances. This is the branch that is gone to if switch 2, EXECUTE, has just been hit. In general, this is determined in step 106. When switch 1 (the ITEM switch) is one in step 107, this is a START (FIG. 4) and switch 1A (FIG. 8) is branched to. But if switch 1 is equal to two, as determined by step 108, the imbalance calibration is started. If the flow calibration has been set as indicated by step 109, then the previous values are cleared in 110, and in step 111 the automatic correction is made. That is, a correction is made for tidal volume imbalances by declaring that the tidal volume out (TVEX) is correct and that tidal volume has an offset which is to be corrected in all future analyis. This correction is made as illustrated in step 111 by subtracting Tidal Volume Out from Tidal Volume In, and using that as an offset to Tidal Volume In in the future. This difference is stored in an indicator called TVEXDS as indicated in step 111.

Figure 11:
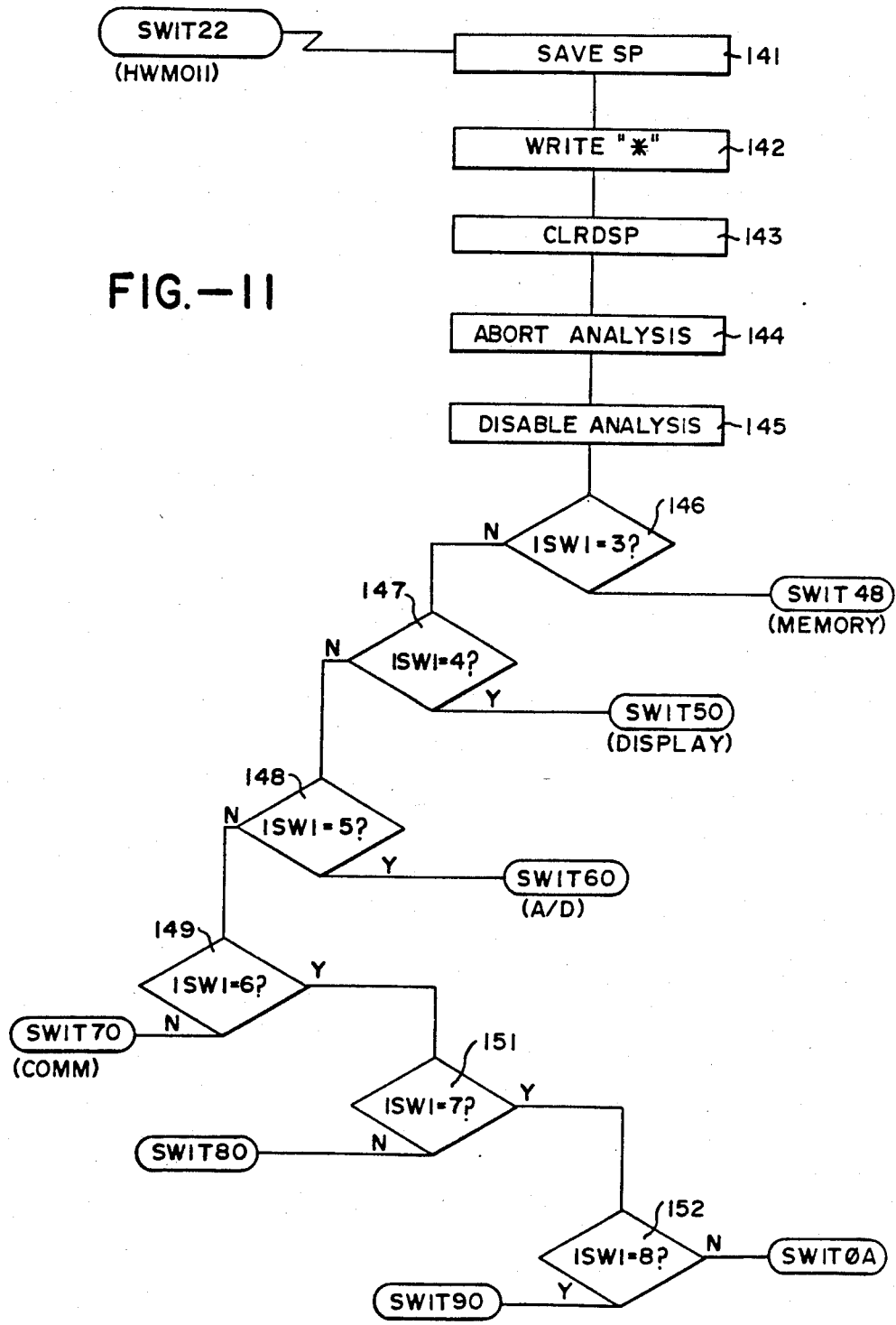

FIG. 11 relates to switch 1C (see step 6, FIG. 7) which is the ALARM mode. In step 121, the inquiry is made if the ITEM switch 1 is set to a legal value. In other words, is it larger than the largest permissible value. If it isn't, then you branch from an earlier place to clear the display. If it is within legal limits, then in step 122, the question is asked "whether switch 2 is equal to zero, one or greater than one." If switch 2 were equal to zero, then the name of the variable is written as indicated by step 123, and the return is made. In step 124, a differentiation between 1 and 2 is made, that is "is switch 2 equal to one." This means that it was pushed once, and that it is desired to start entering a value using the potentiometer 36 on the panel. Thus, the "NO branch" of step 124 is taken and an alarm flag is set in step 126, which states that on the subsequent passage through this item, the panel potentiometer will continue to be read at any analysis that is disabled as stated in step 127 and 128.

Continuing after step 128, the abort analysis, a star (*) in step 131 is written to indicate an execution, step 132 clears the display of the potentiometer value, step 129 initializes the table that gives the gains for each of the various panel alarm settings. That is, each alarm variable maps all possible positions of the alarm potentiometer into some specific range. For example, respiratory rate high (RR HI) alarm is allowed to be set anywhere from 10 to 50. Respiratory rate low (RR LO) alarm is allowed to be set anywhere from 3 to 15. So the limits indicated for each alarm are mapped into the central table. Thereafter, in step 133, this is a sub-routine which reads the value of the potentiometer, converts it to whatever units are appropriate, and displays it.

Now back to step 124, if switch 2, the EXECUTE switch, were greater than one, then in step 134, the current value is loaded and in step 135, the alarm is cleared. In step 136, a second star (**) is written, which indicates that this value has been accepted, SQUELCH is cleared in 137, and in 138, the "data lost" display LED is turned off indicating that some manually entered data has been presented to the computer.

Figure 10:
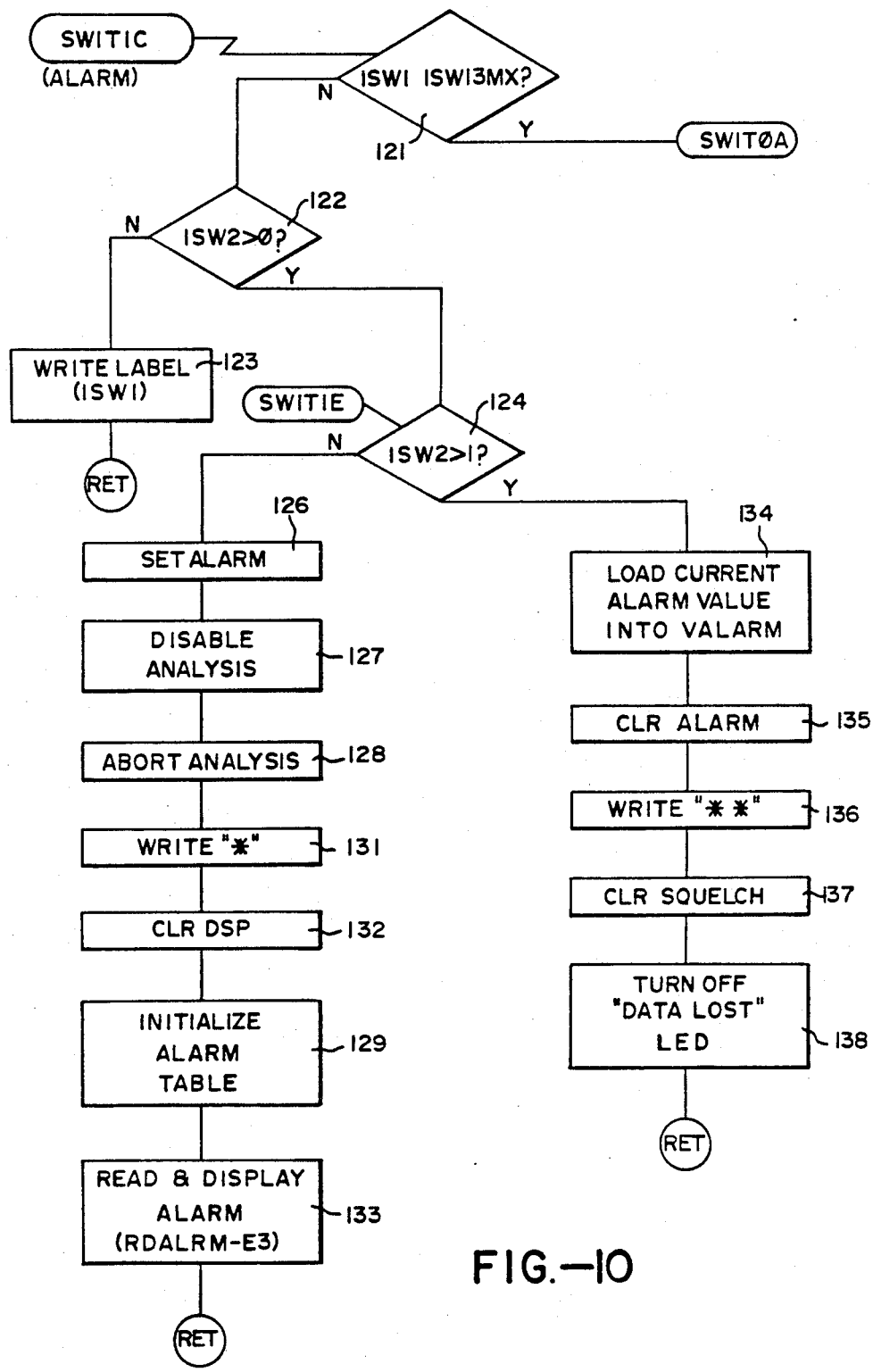

Finally, FIG. 10 is the flow chart for the hardware monitor impelmentation. In the hardware mode, everything else that is going on in the machine is ignored. Thus, referring to FIG. 11, various indicators are saved, so that those conditions can be gone back to. For example, in step 141, the position of the stack is saved. In step 142, a star is written, in step 143, the top of the display is cleared, and in step 144, any analyses that are in progress are stopped and disabled. In step 145 and thereafter in step 146, the question is asked "what is switch 1 equal to." This continues in step 147 through 152. The four switch positions illustrated in FIG. 5 are switch 48 for memory exercise, switch 50 where display is exercised, switch 60 for analog to digital converter exercise, and switch 70 for communications. This relates to switch steps 146 through 149 respectively. Branches 151 and 152 are unimplemented.

Thus, an improved pulmonary monitor and in general a monitor useful where any complex group of physiological variables must be displayed has been provided.

What is claimed is:

1. A monitor for the measurement, analysis and display of physiological data derived from a patient comprising:
   (a) a first transducer for measuring physiological data selected from the group consisting of pressure, temperature, gas concentration, cation and ion concentration, pH, capacitance, displacement, motion, force and flow transducers;
   (b) an analyzer having means for calculating selected physiological characteristics of a patient from said transducer physiological data; and alarm means; and means for displaying said measured physiological data and calculated physiological characteristics; and a manually operated hierarchical selection means for controlling the operation of said calculating and displaying means; and means for calibrating said analyzer in order to substantially eliminate measurement errors; and means to communicate threshold physiological characteristics; and means for comparing said calculated physiological characteristics against said threshold physiological characteristics and activating said alarm means when said threshold physiological characteristics are not satisfied; and
   (c) means for communicating said transducer measured physiological data to said analyzer.

2. A monitor as described in claim 1 wherein said hierarchical selection means further comprises:
   (a) first manually operated selecting means for choosing a mode of operation whereby general machine or physiological functions may be selected for display, each mode having a different set of control functions, each set including specific machine operating parameters or physiological characteristics associated with said selected mode of operation;
   (b) second manually operated selecting means enabled upon selection of a mode, for selecting a control function from said set of control functions for said selected mode of operation; and
   (c) manually engaged means for energizing said calculating means for processing said physiological data into calculated physiological characteristics in response to said first and second selection means.

* * * * *